US011058327B2

(12) United States Patent
Shuster et al.

(10) Patent No.: US 11,058,327 B2
(45) Date of Patent: *Jul. 13, 2021

(54) DETECTING MEDICAL STATUS AND COGNITIVE IMPAIRMENT UTILIZING AMBIENT DATA

(71) Applicant: IDEAFLOOD, INC., Carson City, NV (US)

(72) Inventors: Gary Stephen Shuster, Vancouver (CA); Brian Mark Shuster, Vancouver (CA); Charles Marion Curry, Jr., Fresno, CA (US)

(*) Notice: Subject to any disclaimer, the term of this patent is extended or adjusted under 35 U.S.C. 154(b) by 10 days.

This patent is subject to a terminal disclaimer.

(21) Appl. No.: 16/505,557

(22) Filed: Jul. 8, 2019

(65) Prior Publication Data
US 2019/0336046 A1  Nov. 7, 2019

Related U.S. Application Data

(63) Continuation of application No. 16/017,100, filed on Jun. 25, 2018, now Pat. No. 10,342,463, which is a
(Continued)

(51) Int. Cl.
*A61B 5/024* (2006.01)
*A61B 5/00* (2006.01)
(Continued)

(52) U.S. Cl.
CPC .......... *A61B 5/1123* (2013.01); *A61B 5/0024* (2013.01); *A61B 5/0077* (2013.01); *A61B 5/082* (2013.01); *A61B 5/112* (2013.01); *A61B 5/18* (2013.01); *A61B 5/4803* (2013.01); *A61B 5/4845* (2013.01); *A61B 5/4863* (2013.01);
(Continued)

(58) Field of Classification Search
USPC .................................................. 600/300–301
See application file for complete search history.

(56) References Cited

U.S. PATENT DOCUMENTS

2008/0292151 A1* 11/2008 Kurtz ..................... G16H 15/00
382/128
2009/0234916 A1*  9/2009 Cosentino ............ A61B 5/0538
709/203
(Continued)

*Primary Examiner* — Nicole F Lavert
(74) *Attorney, Agent, or Firm* — Sherrie Flynn; Coleman & Horowitt LLP

(57) ABSTRACT

Devices for determining the likelihood that a user of a primary monitoring device ("PMD") has developed a medical condition, generally comprising sensors coupled to the PMD, wherein the PMD detects changes to sensor readings over time, and wherein the changes indicate a change in the likelihood that a user of the PMD has developed a medical condition. In some embodiments, motion sensors are operably coupled to the PMD, and the PMD monitors and saves data relating to characteristics of motion detected, which are used to determine whether there has been a change in a likelihood that a user is undergoing a medical event. In further embodiments, the PMD comprises cameras, and the PMD monitors and saves data relating to movement of a user's eyes, which is utilized to determine whether there has been a change to a likelihood that the user is currently undergoing a medical event.

18 Claims, 6 Drawing Sheets

Related U.S. Application Data continuation of application No. 14/658,074, filed on Mar. 13, 2015, now Pat. No. 10,004,431.

(60) Provisional application No. 61/952,792, filed on Mar. 13, 2014, provisional application No. 61/952,799, filed on Mar. 13, 2014, provisional application No. 61/952,781, filed on Mar. 13, 2014, provisional application No. 61/952,759, filed on Mar. 13, 2014, provisional application No. 61/952,788, filed on Mar. 13, 2014.

(51) Int. Cl.
*A61B 5/11* (2006.01)
*A61B 5/18* (2006.01)
*A61B 5/08* (2006.01)
*G06F 16/245* (2019.01)
*G06F 16/951* (2019.01)
*G10L 25/66* (2013.01)
*G06T 19/00* (2011.01)
*G10L 15/01* (2013.01)

(52) U.S. Cl.
CPC .......... *A61B 5/6898* (2013.01); *A61B 5/7246* (2013.01); *G06F 16/245* (2019.01); *G06F 16/951* (2019.01); *G06T 19/006* (2013.01); *G10L 25/66* (2013.01); *A61B 5/002* (2013.01); *G10L 15/01* (2013.01)

(56) References Cited

U.S. PATENT DOCUMENTS

| | | | | |
|---|---|---|---|---|
| 2011/0015496 | A1* | 1/2011 | Sherman | A61B 8/56 600/301 |
| 2013/0179188 | A1* | 7/2013 | Hyde | G06Q 10/10 705/3 |
| 2013/0262155 | A1* | 10/2013 | Hinkamp | G06F 19/00 705/4 |

* cited by examiner

DETECTING MEDICAL STATUS AND COGNITIVE IMPAIRMENT UTILIZING AMBIENT DATA

CROSS-REFERENCE TO RELATED APPLICATIONS

This application claims priority to and is a continuation of U.S. patent application Ser. No. 16/0117,100, filed Jun. 25, 2018, now issued as U.S. Pat. No. 10,342,463, which is a continuation of U.S. application Ser. No. 14/658,074, filed Mar. 13, 2015, now issued as U.S. Pat. No. 10,004,431, which claims priority pursuant to 35 U.S.C. § 119(e) to and the benefit of U.S. Provisional Patent Application Nos. 61/952,759, 61/952,781, 61/952,788, 61/952,792 and 61/952,799, all filed Mar. 13, 2014. The text and contents of each of these applications are hereby incorporated into this application by reference as though fully set forth herein.

FIELD OF INVENTION

The subject disclosure generally relates to the field of medical and cognitive impairment. Specifically, embodiments of the present invention relate to systems, methods and devices for estimating the likelihood and level of medical or cognitive impairment of a person, and methods for calibrating devices to measure the medical or cognitive impairment of a person.

DISCUSSION OF THE BACKGROUND

For the purposes of this specification, the present invention will generally be described in relation to impairment caused by alcohol, drugs and medical conditions. However it should be understood that the invention is not so limited, and may be applied and/or used to detect impairment in a wide variety of other applications, including but not limited to impairment due to toxic chemicals in the environment, chemical imbalances in body, changes to mental status, insufficient sleep, changes to blood sugar levels, divided attention, vision changes, hearing changes, use of a mobile device while walking or using a vehicle, and/or other similar causes.

Humans have developed a society in which certain drugs (e.g., alcohol and prescription medications) are legal. There are restrictions on the use of these drugs, and legal ramifications for exceeding the bounds of the law. Whether a human is within the legal limits of drug use or not, the consumer of the drug may experience effects of the drug. While there are other physiological ramifications for drug use, the observable performance effect that humans perceive in the drug consumer are a result of the effect that the consumed drug has on the chemistry of human brain. For instance, alcohol affects the brain by decreasing brain activity using an inhibitory neurotransmitter. Concurrently alcohol causes an increase in dopamine production resulting in a feeling of pleasure. The inhibitory effects of alcohol affect the parts of the brain responsible for movement, balance, sensory perception, reason and memory.

For humans that have developed a dependence or addiction to drugs such as alcohol, rehabilitation programs are available. Additionally, if a person is brought up on charges for driving under the influence the offender may find themselves on parole. The offender may also be ordered to wear an ankle monitor, or a SCRAM bracelet that is able to detect alcohol consumption. Breathalyzers and/or ignition interlocks are installed in the vehicles of some offenders. Currently available to many consumers are blood alcohol content calculating systems for mobile devices to allow consumers to calculate whether or not the user has reached the legal limit.

What does not exist in the art is a system or method for leveraging the sensors of a mobile device, such as a smartphone, to detect the perceived or actual intoxication of a human using the system or mobile device. In this digital age, mobile devices are taken with consumers everywhere they go. Mobile device users are constantly interacting with their devices and even when they are not, the device is constantly sending, receiving and collecting data. Mobile devices have already proven to be useful in athletic training and tracking, and these devices find more uses in the medical field every day.

In particular, drugs and alcohol are a significant public health problem. Many crimes, accidents, and injuries result from chemical impairment. Undesirable behavior frequently presents itself when humans are inebriated because many drugs, including alcohol, impair the function of the cerebral cortex of the frontal lobe, which is responsible for the processing of information prior to acting. Some animals, such as cats, are without this portion of the brain and, as a result, immediate reaction to an action is observed in these species. In a state of inebriation, a human may have slower than usual reaction times as their ability to process information decreases.

In addition, people may have reduced judgment when they are under the influence of alcohol or drugs, immediate irrational reactions once they are severely inebriated and/or other impairments. Indeed, in some cases, the undesirable behavior includes the act of consuming the impairing chemicals. Moreover, impairment can occur without the involvement of any chemicals, such as in the case of changes to mental status, insufficient sleep, medical problems, changes to blood sugar levels, divided attention, vision changes, hearing changes, use of a mobile device while walking or using a vehicle, and other causes. It should be appreciated that while this document references alcohol and chemical impairment, the inventions may be applied to other forms of impairment as well, such as the ones in the preceding sentence, traumatic brain injury, excessive fatigue, stroke damage, and other similar impairments.

Many people have had the experience of observing a friend or another individual become intoxicated and witnessed the change and the events that may lead up to life altering mistakes. On the other hand, once these mistakes have been made and the offender is then mandated by the state to reform, a monitoring system must be put in place to ensure that the judgment against the offender is upheld. In an effort to overcome this monitoring system, some offenders remove tracking devices and employ various schemes to obfuscate biological tests. In the midst of these efforts, it is often the case that, like most other people, these offenders keep a mobile device, such as a smartphone, with them nearly all of the time. Indeed, in some cases the monitoring and/or abstinence is voluntary, such as a person who is a recovering addict.

Due to the potential inability of a person to self-monitor or be accurately monitored by a friend, and the ability of penal monitoring systems to be foiled, at minimum it is desirable to employ a secondary system to monitor inebriation.

Applications also present in the medical field. After a procedure, patients are often prescribed pain killers containing codeine, Tylenol 3, or opiates that encumber the patients' ability to operate machinery such as a motor vehicle. While not severely intoxicated, patients under these circumstances could benefit from a personal monitoring system that aids the user in detecting a change in their normal performance. Prescription and other medications often come with a warning about the risk of impairment.

Finally, compliance with recommended medical testing is often difficult to obtain. Indeed, active participation in medical testing or monitoring is sometimes avoided because of the subconscious fear of a negative diagnosis. Therefore, it is desirable to perform medical diagnoses without the need for patients to take significant action or employ specialized equipment or tests.

There are significant public health and safety benefits to simplifying the detection of impairment, whether caused by alcohol, drugs, other chemicals, mental status changes and/or medical issues. Existing methods and devices for determining impairment rely on specialized diagnostic tools, examination by specialists, or a combination of these methods. Consent to testing or examination is often difficult to obtain, and compliance with recommendations that testing or examination be done is often poor.

Consequently, there is a strong need for methods and devices that detect medical and/or cognitive impairment without the need for specialized devices, examination by specialists, consent of the person being evaluated, and compliance with recommendations to be examined. To this end, it should be noted that the above-described deficiencies are merely intended to provide an overview of some of the problems of conventional systems, and are not intended to be exhaustive. Other problems with the current state of the art and corresponding benefits of some of the various non-limiting embodiments may become further apparent upon review of the following description of the invention.

SUMMARY OF THE INVENTION

Embodiments of the present invention relate to methods and devices for determining the likelihood that a person is impaired and estimating the level of impairment of a person. The methods may be applied, at minimum, to determining the likelihood that a person is impaired due to alcohol, drugs, exposure to toxic chemicals, changes to mental status, insufficient sleep, medical problems, changes to blood sugar levels, divided attention, vision changes, hearing changes, use of a mobile device while walking or operating a vehicle. Other methods, devices and systems for accomplishing similar objectives are disclosed in the co-pending application, Ser. No. 14/657,303, entitled "Systems, Devices and Methods for Sensory Augmentation to Achieved Desired Behaviors or Outcomes," filed concurrently by the inventors hereof, which is hereby incorporated by reference into this application as if fully set forth herein.

A system for detecting and approximating how intoxicated a human is becoming can be useful in the consumer market, medical field and rehabilitation services. For example, due to the rhythmic nature of some aspects of human activity such as walking and talking, the actions produce a wave-like function that can be measured and recorded using sensors on mobile devices. These activities are directly affected by drug use, and as a result, how a human normally walks and talks, for instance, may be compared to how the same person performs these same activities under the influence. Based on the data and the comparison of that data to "normal" or "baseline" data, the system may notify the user or system administrator of what may be signs of intoxication.

This ability to install a system that can tell users how drunk they may appear may be useful for consumers, professionals and institutions alike. Such system may be useful and easily configured for different markets. The system may be useful to users who want to be responsible while consuming legal drugs, and desire some assistance in monitoring themselves as they use. The system may be useful to those consumers who have identified a personal addiction problem. The system may also be useful to rehabilitation facilities and law enforcement agencies. The system may be ideal as a supplement to monitoring systems for parolees. The notification aspect of the system further enhances its utility as the system may notify a parole officer of a violation, a sponsor of a relapse or a friend of another friend in need. Such notification may be accomplished, among other mechanisms, via push notification.

In some aspects, a compelling feature of the present invention is that the mobile device has become so ubiquitous in society that for the vast majority of people, their devices have become an extension of them. The presence of a passive health and intoxication monitoring system on these ever-present devices has the ability, at minimum, to inform users of their state of intoxication and, at maximum, save lives by disabling the cars of intoxicated drives and notifying friends.

Consumer devices have access to a remarkable amount of data measurable by the sensors natively present in them and the user data that the devices process. By analyzing the data and comparing it to known or learned data patterns, the likelihood that a user is impaired and/or medically at risk may be evaluated. By gathering and analyzing ambient data, a smartphone determines a "normal" data set for a user. Deviation from that data set is an indication of a possible problem. For example, if the motion sensing chip data indicates that a user's gait has steadily become worse over the course of an hour while the user was, according to the GPS, proximate to a bar, the device may determine a likelihood that the user is inebriated. Changes to speech, sleep patterns, time spent interacting with the device, the number of errors the user makes typing on the device, and other data are utilized to determine the likelihood of a medical, mental or toxicological impairment without the need for specialized equipment or tests.

In one embodiment, the invention relates to a method of estimating the impairment of a person, the method comprising (a) gathering ambient data from one or more sensors operably coupled to a primary measuring device (PMD); (b) analyzing/identifying the data gathered; (c) querying at least one data base to identify baseline data regarding the person; and (d) comparing the ambient data to the baseline data to determine a likelihood that the person is impaired. In some embodiments, the method may further comprise (e) gathering data from one or more external devices, and (f) comparing the external device data to the baseline data to further determine the likelihood that the person is impaired. The one or more external devices may comprise, among other items, a motion-sensing watch, a head-mounted camera and/or a medical measurement device. The sensors may comprise a fingerprint sensor, an accelerometer, a three-axis gyroscope, an orientation sensor, an assisted GPS sensor, as well as others. In some embodiments, the method may further comprise a voice-to-text analysis of the person's speech, and/or identifying predictable causes to changes in ambient data to confirm or modify the likelihood that the person is impaired.

The invention also relates to a method of calibrating a PMD, the method comprising (a) gathering calibration data about a person during one or more calibration periods; and (b) analyzing the calibration data to determine baseline data for the person, wherein the baseline data is configured to be compared against ambient data to determine a level of impairment of the person. In some embodiments, the method may also comprise (c) operably coupling a breath alcohol measuring device to the PMD, and (d) calibrating the PMD using the alcohol level measured by the breath alcohol measuring device. In some instances, the method may also comprise (e) generating one or more profiles, and (f) comparing the ambient data to the profile(s) to further determine the level of impairment of the person, wherein the profiles are generated by analyzing data associated with one or more other persons with known or highly likely states of impairment.

The invention further relates to devices to estimate the impairment of a person, the device comprising (a) one or more sensors operably coupled to a first PMD, the sensors configured to capture ambient data about a person, wherein the first PMD is configured to query at least one data base to identify baseline data and compare the ambient data to the baseline data to determine the likelihood that the person is impaired. In some embodiments, the first PMD may also share ambient data with a second PMD and the second PMD may be configured to process the ambient data shared by the first PMD. In yet other embodiments, the first PMD may be configured to transmit notifications to one or more predetermined contacts.

Embodiments of the present invention advantageously provide methods, systems and devices for estimating the impairment of a person, without the need for sophisticated medical equipment and/or specialized diagnostic tools, examination by specialists, or some combination thereof. Embodiments of the present invention also advantageously provide methods and devices for determining the impairment of a person without the consent of the person being evaluated and/or compliance with recommendations to be examined.

These and other advantages of the present invention will become readily apparent from the detailed description below.

BRIEF DESCRIPTION OF THE DRAWINGS

Various non-limiting embodiments are further described with reference to the accompanying drawings in which.

DETAILED DESCRIPTION

Figure 1:
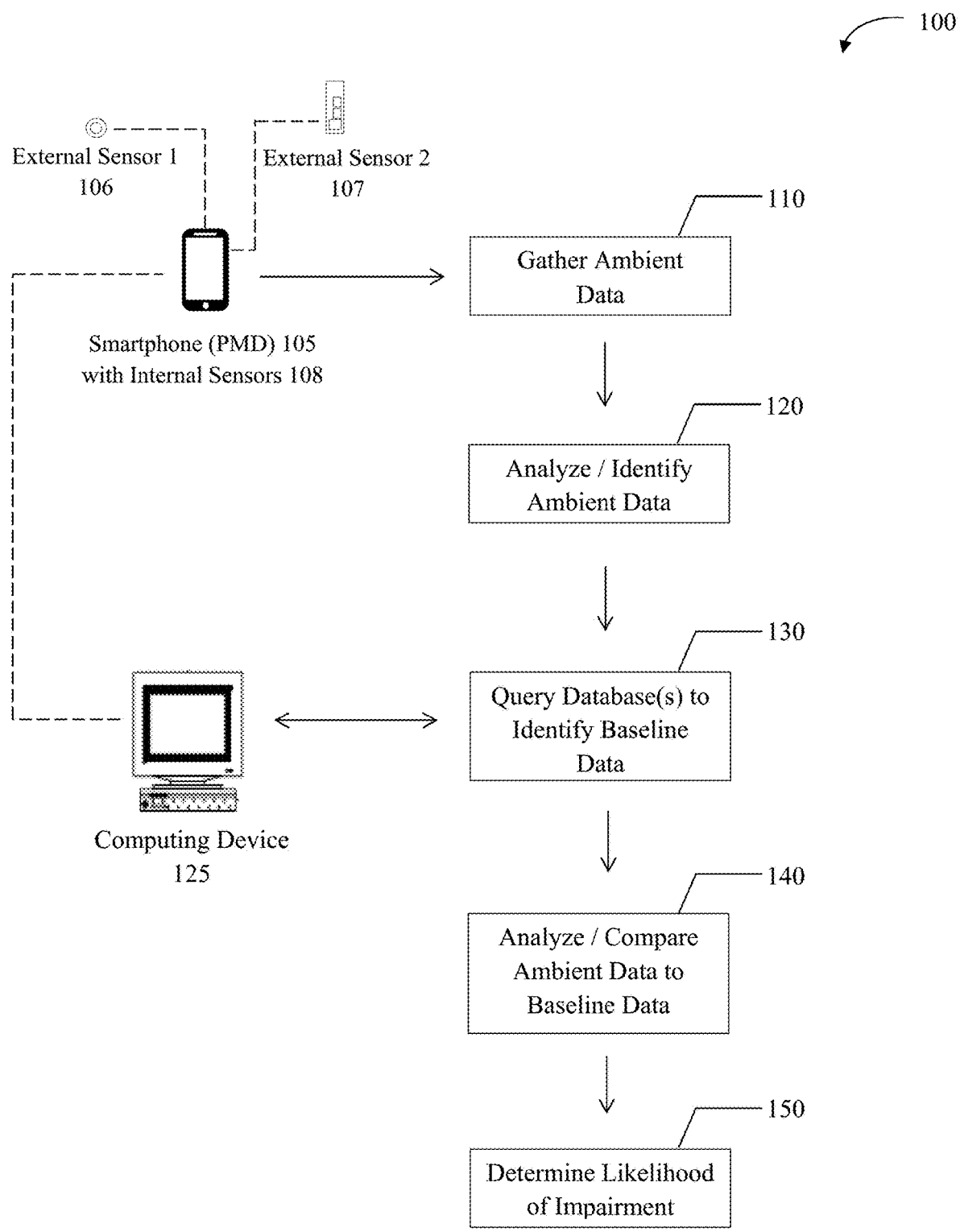
FIG. 1 schematically illustrates a method of determining the likelihood of impairment of a person according to an embodiment of the present invention.

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications, and equivalents that may be included within the spirit and scope of the invention as defined by the appended claims. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures and components have not been described in detail so as not to unnecessarily obscure aspects of the present invention. These conventions are intended to make this document more easily understood by those practicing or improving on the inventions, and it should be appreciated that the level of detail provided should not be interpreted as an indication as to whether such instances, methods, procedures or components are known in the art, novel, or obvious.

For the sake of convenience and simplicity, the terms primary measuring device (PMD), smartphone, device, and mobile device may be used interchangeably herein, but are generally given their art-recognized meanings. Also, for convenience and simplicity, the terms user, subject person, consumer, and person may be used interchangeably, and wherever one such term is used, it also encompasses the other term.

As discussed in the background, there is a strong need for methods and devices that detect medical and/or cognitive impairment without the need for specialized devices, examination by specialists, consent of the person being evaluated, and compliance with recommendations to be examined. The present invention relates to methods, systems and devices for estimating the impairment of a person, without the need for such sophisticated medical equipment, special diagnostic tools and/or examination by specialists, or some combination thereof. Embodiments of the present invention also advantageously provide methods, systems and devices for determining the impairment of a person without the consent of the person being evaluated.

Measurements of fine motor control, balance, speech slurring, speech patterns and intonation, vital signs, nystagmus, pupil size, activity, lack of activity and response times can generate a fairly accurate approximation of a user's level of intoxication and/or health. Similarly, location, word choice, behavior, amount and type of movement, frequency of bathroom use, changes to interactions with mobile devices, error rates in using mobile devices, types of responses to communications (e.g., screening phone calls), and proximity to certain other mobile devices or persons are all elements that may be associated with certain behaviors or conditions. Through calibration and/or artificial intelligence, a device may differentiate between a user's sober and inebriated behavior and motor functions, as well as identify behavior or changes to user behavior that may indicate medical problems. Indeed, in one aspect, the level of impairment and/or the level of medical risk may be approximated.

For purposes of this discussion, the term "primary measurement device" ("PMD") refers to a device, in some cases a smart phone, that contains one or more sensors. Although the invention is often discussed here with reference to a smart phone, it should be understood that other devices may be included as well. For example, Google Glass®, which is technically not a smart phone, has numerous sensors that would allow it to be utilized with regard to certain aspects of the present invention. Further, this document references a "mobile" device, but the mobility of the device is not necessarily required for at least some aspects of the invention.

The primary measurement device may also be operably coupled, on a temporary or permanent basis, with additional devices, such as a motion-sensing watch, a head-mounted camera, or a specialized medical device such as the Scandau Scout. The PMD may also be coupled with one or more separate or integral processing units, and such coupling may be achieved directly, over a near field network (e.g., a Bluetooth), a local area network, (e.g., a WiFi network), a cellular network, a wide area network, or otherwise.

There are a variety of sensors that are standard equipment on PMD's. Taking the Apple iPhone 5 as an example, the sensors (listed by function, whether or not their readings are generated by the same physical chip) include: a fingerprint sensor; an accelerometer; a three-axis gyroscope; a compass; an assisted GPS; a front facing camera (and associated sensors); a rear facing camera (and associated sensors); a microphone; a digitizer (touch screen); an orientation sensor; cellular voice data; cellular data; WiFi data; Bluetooth data; a charging sensor; a battery measurement sensor; an ambient light sensor; a magnetometer; and a proximity sensor.

PMD's may additionally be equipped with a variety of other sensors, including, but not limited to: a wireless charging device (and associated sensors); terrestrial/RDS/satellite radio sensors; pressure sensors; temperature sensors; humidity sensors; NFC communications sensors; face and object detection (often within software supporting camera); and/or barometric pressure sensors. PMD's may also have output capability, such as a light, that maybe used to enhance data gathering by seasons. Further, PMD's may also have output capabilities, such as a light, which may be used to enhance data gathering by sensors.

PMD's may also receive, store, and send data, such as data generated as a result of interne usage, SMS usage, or other device usage. The search and browsing history and/or text email data may be used to provide hints to the PMD as to what impairment to test the user for, or to provide a basis to change the scaling of risks of impairment or illness. In some cases, the data may include data generated by specialized devices or examinations, such as that generated by the Scandou Scout or a breath alcohol measurement device.

Chemical, mental state and medical impairment share many characteristics, and the description of these inventions in the context of one form of impairment should be understood to apply to the others as well. Because alcohol impairment is a fairly universal common point of reference, alcohol impairment will be used frequently for purposes of illustration. However, this should not be construed as limiting, as the methods and devices described herein apply to other chemical, mental and medical impairment as well.

Exemplary Systems and Methods of Determining the Level of Impairment

In one implementation, a method of determining the level of impairment of a person comprises (1) gathering ambient data from one or more of the available data sources operably coupled to a primary measuring device (PMD); (2) analyzing and identifying the ambient data; (3) querying at least one data base to identify baseline data regarding the person; (4) comparing the ambient data to the baseline data, and (5) determining the likelihood that the person is impaired. An embodiment of the method is shown schematically in FIG. 1.

In the embodiment of FIG. 1, smartphone (PMD) 105, having a plurality of internal sensors 108, is operably coupled to a first external sensor 106 and a second external sensor 107, and also to a computing device 125. Although in the embodiment of FIG. 1, the PMD 105 is a smartphone, the PMD 105 may be another device, such as a tablet, a notepad, a laptop, a personal digital assistant (PDA), or other devices, such as wearable ubiquitous computing devices (e.g., Google Glass®), etc. The plurality of internal sensors 108 may comprise a fingerprint sensor, an accelerometer, a three-axis gyroscope, a compass, an assisted GPS, a charging sensor, a battery measurement sensor, an ambient light sensor, a magnetometer, an proximity sensor, an orientation sensor, one or more biometric sensors, etc. Other data collection devices may also be integral to the PMD 105. For example, the PMD may also comprise a front facing camera (with associated sensors), a rear facing camera (with associated sensors), a microphone, a digitizer (e.g., a touch screen), etc. Further, the PMD 105 may have capabilities to capture other data, including, but not limited to cellular voice, cellular data (e.g., usage history), Wi-Fi data and/or Bluetooth data, and store and/or transmit data.

The PMD 105 may optionally be equipped with one or more of a variety of other sensors, including, but not limited to a wireless charging station (and associated sensors), terrestrial/RDS/satellite radio sensors, pressure sensors, temperature sensors, humidity sensors, NFC communications sensors, face and object detection devices (e.g., within software supporting camera), and/or barometric pressure sensors.

Each of first and second external sensors 106, 107 may be one of the many types of sensors listed above as sensors possibly internal to the PMD 105, except that external sensors 106 and 107 reside external to the PMD. In some instances, these external sensors already exist in the subject environment (e.g., temperature, humidity sensors may exist in temperature controlled environments) and these external sensors may be leveraged for data collection where appropriate. Additionally, and although not shown in the embodiment of FIG. 1, external measurement devices may also optionally be coupled to PMD 105. Such external devices may include, but are not limited to devices to measure, blood alcohol level, blood sugar level, blood pressure, heart rate, activity level, calorie consumption, etc.

In the embodiment of FIG. 1, the PMD is operably coupled to a computing device 125, in which data may be analyzed, identified and/or stored. However, in other embodiments, the data may be analyzed, identified and/or stored on PMD 105 and/or PMD 105 may be operably coupled to one or more servers or other computing/storage devices (e.g., a laptop, notepad, tablet, zip drive, thumb drive, CD ROM, DVD, etc.) from which the PMD may pull useful data.

The method 100 of FIG. 1 begins at step 110, where ambient data is gathered from internal and/or external sensors/devices. At step 120, the data is analyzed and/or identified (e.g., by image, sound, odor, chemical and/or tactile recognition software). At step 130, one or more databases are queried to identify baseline data for the person for whom the level of impairment is to be determined. At step 140, the ambient data is analyzed and compared to the baseline data, and at step 150 the likelihood that the person is impaired is determined.

In one aspect, device data may be utilized to generate a likelihood that the user is impaired, such as GPS data indicating that the user is in a bar, voice-to-text analysis that indicates the user is discussing current impairment or alcohol consumption, camera data showing that the user is consuming alcohol, or other data. In one aspect, the user's likely blood alcohol level may be estimated by analysis of the data (e.g., visual data) to determine the amount of alcohol consumed, the amount of food likely present in the user's stomach, etc. Other factors relevant to medical models for alcohol absorption and metabolism, such as the user's percentage of body fat, weight and gender, as well as the amount of time since the user started drinking, may be identified as well.

Similarly, where ambient data exists that would directly (or nearly directly) indicate the user's level of impairment, such data may be used both to determine the actual level of impairment and to calibrate how the system utilizes other data to determine impairment for past or future periods. An example is that the user blows into a keychain-mounted breathalyzer and the results are observable by the device (e.g., by a camera mounted on the device).

In some embodiments, additional measurement devices may be utilized with or without the permission of the user of the PMD or the additional devices. The data generated by the additional devices may be gathered in whatever manner in which the additional device makes the data available. In one aspect, the data may be obtained utilizing analog to digital data sensors (such as a CCD or CMOS camera) that, in many aspects, obtain the data in the same way it is intended to be obtained by a user of the additional device. For example, a blood pressure monitoring cuff may have no networking capability at all, but does present data via a display for perception by the human eye. By imaging the display, the PMD effectively becomes a data recipient for the additional device. It should be further appreciated that the additional data may take the form of data generated entirely without computer involvement, such as street signs (for location data), a manual thermometer (for temperature data), or a clock (for time data).

In another aspect, multiple PMD's may share data, such as video streams. Such sharing may be of raw data, of data processed to indicate certain information, or a combination. In one example, two people may each be wearing a PMD with hardware similar to Google Glass®. The second PMD would have a direct camera view of the user of the first PMD. The second PMD may share a direct video stream.

In some cases, such as where bandwidth is limited, or where there is no bandwidth, data may be stored until a network connection is established. Where the permissions between the two PMD's indicate that raw data is not to be shared, or otherwise, the second PMD may process the data (e.g., user of PMD 1 just took a drink of Coors Light® beer, the container volume is 12 ounces, the container was 68% full previously, and the container is now 60% full). In some aspects, the first PMD may tell the second PMD what kind of data it needs. For example, the first PMD may indicate that it needs to know whether the person is consuming drinks purchased by another, so that the first PMD may more accurately record the amount of alcohol the person in consuming.

In another aspect, there may be a database which the second PMD may consult to identify the data. For example, if the person is at a drinking establishment with a group of friends, the second PMD may access one or more databases to identify the individuals within the group. This aspect may be useful in a situation where a notification of the level of intoxication of a person is to be sent to at least one of several friends. The second PMD may identify that only one friend in the notification group is not participating in the current consumption of alcohol, and may notify the non-participating friend to be on standby for notifications.

In another aspect, a payment may be made, or a credit useful for something of value may be created, in favor of a PMD that performs a task on behalf of a user of another PMD. Pooled or shared media, social network status updates, and other data sources may be utilized as well, for example, to identify useful information about the person or person's network of friends, or to accept credits or payments for the tasks performed by non-primary PMD's.

Whether calibrated against known periods of intoxication or not, the PMD 105 may analyze the data available to determine "normal" or "standard" baseline data for a user. For example, the user's gait, the speed of the user's pupillary constriction when transitioning from a dark to a brighter environment, the speed and/or auditory volume of a user's breathing, the rate at which the user blinks, the frequently of high acceleration events and/or other measurements are likely to fall within one or more sets of regularly observed patterns. Such patterns may be segregated by time of day, by location (e.g., gait at the gym is likely to differ from gait at home), by the task the user is doing (e.g., the user's frequency and rate of eye movement is likely to differ when playing a fast-moving video game than when watching the evening news), etc. In one aspect, a set of standard measurements may be generated and a set of exceptions may be generated, the set of exceptions optionally generated at least in part by the segregated patterns.

In one aspect, predictable causes of changes to behavior may be identified and accounted for in data analysis. For example, a premenopausal woman may experience a monthly cycle that includes hormonal changes, changes to facial and soft tissue symmetry, changes to the number of visits to the restroom, and the potential presence of blood in the toilet (which, for a male user, may be an indicator of a medical problem that a camera-based data source for a PMD might detect). Another cyclic cause of change is the work week when compared to the weekend.

Figure 2:
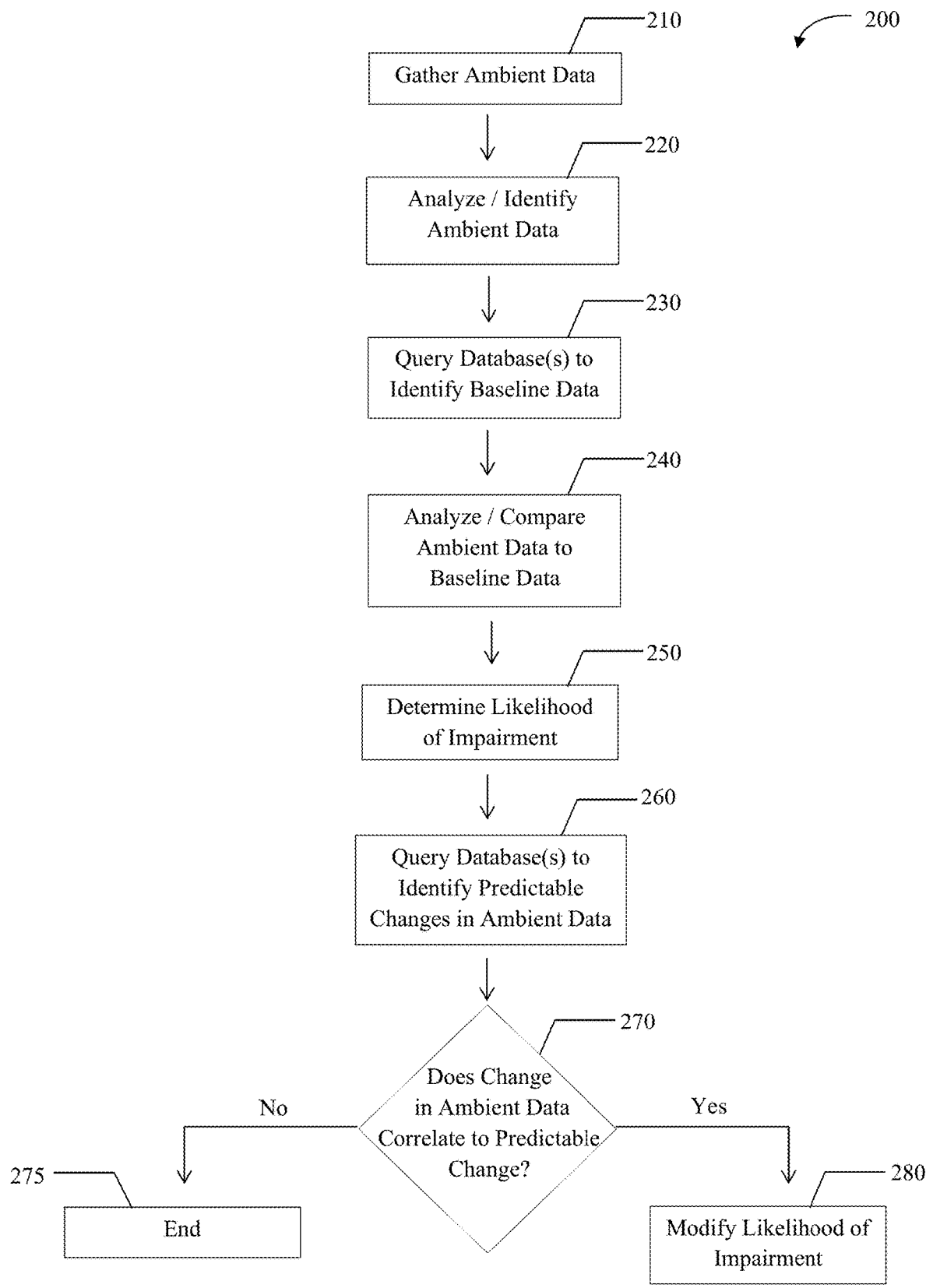
FIG. 2 schematically illustrates schematically illustrates a method for determining and modifying the likelihood of impairment based on predictable changes to the ambient data of a person according to an embodiment of the present invention.

One aspect of the present invention includes a method for accounting for predictable changes in behavior when analyzing the likelihood that a person is impaired. Such aspect is schematically illustrated in method 200 of FIG. 2. Method 200 begins at step 210, where ambient data about a person is gathered. The ambient data may be gathered by any number of different sensors (both internal to a PMD and/or external), and/or devices which provide additional ambient/medical data as is described above.

At step 220, the captured data is processed and images, sounds, odors, etc. are identified (e.g., by image, sound, odor, chemical and/or tactile recognition software). At step 230, one or more databases are queried to identify baseline data about the user. At step 240 the ambient data is analyzed and compared to the baseline data. At step 250, based upon the comparison of step 240, the likelihood of impairment is determined. The method then proceeds to step 260, wherein one or more databases are queried to identify predictable causes and/or changes in ambient data. At step 270, a determination is made as to whether the ambient data correlates to a predictable change. If "no" then the method ends at step 275, and the initially determined likelihood of impairment is the final determined likelihood of impairment. If, instead, the determination made at step 270 is that "yes," the ambient data correlates to a predictable change, then at step 280, the likelihood of impairment is modified based on the predictable change in ambient data.

In one aspect, data analysis (e.g., at step 140 in method 100 of FIG. 1, or at step 240 in method 200 in FIG. 2) may be accomplished using algorithms similar to those used by email filtering systems, such as the Gmail™ spam filtering system. Using such a system as an analogy, providing data generated during periods of known intoxication may be superficially similar to seeding the system or correcting the system in a manner superficially analogous to manually identifying spam and non-spam emails. However, the system may function without such seeding, and, over time, may reach an accuracy level nearly identical to that possible with seeding.

In one aspect, Bayesian filtering or other data analysis may be done whereby data associated with one or more people with known (or likely, or highly likely) conditions or states of intoxication are utilized to generate profiles that can be used to measure the likelihood that a different user is experiencing similar conditions. In another aspect, the changes between baseline readings for one or more people with known (or likely, or highly likely) conditions or states of intoxication and their readings when experiencing the effects of the conditions or states of intoxication may be utilized to generate a profile for changes in readings from baseline (or otherwise) that indicate a probability that a user is experiencing a similar condition or state of intoxication.

Figure 3:
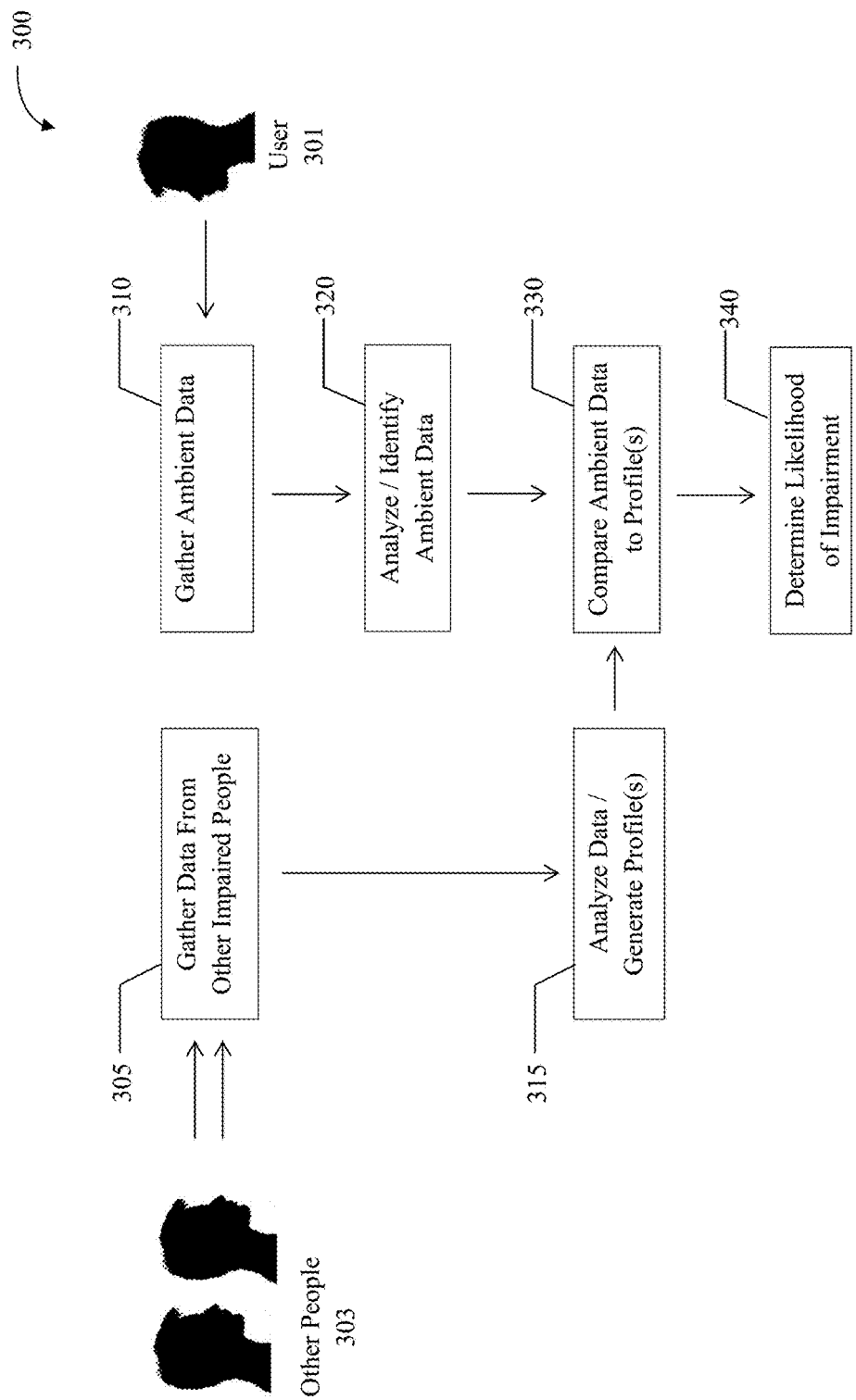
FIG. 3 schematically illustrates a method for determining the likelihood of impairment of a person based on profiles generated by other impaired persons according to an embodiment of the present invention.

Referring now to FIG. 3, therein is shown a schematic representation of a method 300 in which one or more profiles generated from other people 303 are utilized to determine the likelihood of impairment of a user 301. Method 300 starts at step 305, wherein data is gathered from other people 303 with known or highly likely impairments. Such data may be gathered using one or more of the internal/external sensors and/or devices described above for methods 100 and 200. At step 315, the data is analyzed and profiles are generated based on such data. Such profiles may correlate the data gathered from the other people 303 with the intoxication level of such other people 303.

At step 310, ambient data about the user 301 is gathered. As with step 305, the ambient data may be gathered using one or more of the internal/external sensors and/or devices described above for methods 100 and 200. At step 320 the ambient data is analyzed and/or identified (e.g., by devices and methods described above for FIGS. 1 and 2). It should be noted that steps 310 and 320 may be performed after or simultaneously with steps 305 and 315. Typically, steps 305 and 315 will be performed before ambient data about the user 301 is gathered (before step 310), and the resultant profiles will be stored in one or more databases for future access. Any number of profiles may be generated, and each such profile may be generated from one person, or by averaging the data from a plurality of persons.

At step 330, ambient data about the user 301 is analyzed and compared to the profiles generated from the other users 303. Then, at step 340, the likelihood that the user is impaired is determined from the comparison to the profiles. In some instance, not only is the likelihood of impairment determined, but also the level of impairment. For example, in reference to impairment due to alcohol consumption, the system may indicate that the person is slightly impaired, but likely under the legal BAC limit for operating a motor vehicle, or that the person is very impaired at a level likely twice the legal BAC limit for operation of a motor vehicle.

The set of other users 303 utilized to generate the profile(s) may, in some aspects, be selected based on similarities to the user 301 being evaluated. For example, evaluation of a male user in his mid-20s who weighs 200 pounds and is 5'10" tall may result in creation of one or more profiles based on data for other users who share the same or similar characteristics.

In certain aspects, confidence intervals may be utilized. For example, it may be desirable to require a 2 sigma deviation over one episode or a 1 sigma deviation over ten different episodes before indicating that the user 301 should be tested, for example, for inner ear balance issues. In another example, the duration of male urination may be required to be a 1 sigma deviation 5 times or 2 sigma deviations 2 times before taking action based on risk of prostate enlargement, particularly when the urination sound is weaker or quieter or starts and stops or takes longer than expected to stop.

In one aspect, biometric and similar data may be utilized to verify the identity and/or identify the activities of the user 301. For example, the inventions may monitor purchases via near field communication, snooping via Wi-Fi unencrypted packets in promiscuous mode, or other similar mechanisms/methods. In one aspect, monitoring may focus on purchases of health-related and/or unhealthy items (e.g., alcohol), and may be utilized as additional data to measure and/or determine impairment to health. Utilizing the alcohol purchase example, such data may be utilized to improve the prediction and measurement of how intoxicated a user is likely to be. When, for example, purchases are made via a purchasing/spending app or function of the PMD, banking data is available on the PMD, and/or the PMD receives an authentication request (e.g., by SMS) to confirm a purchase is legitimate, such data may also be utilized in determining the likelihood that the user is impaired. In addition, data from financial transactions, insurance claims, GPS, and other sources may be correlated with pictures, social media, and other data sources to determine or approximate the mental state the user was likely in at the time certain measurements were made and/or purchases detected.

Exemplary Methods of Calibrating a PMD to Determine Impairment

The present invention also relates to a method of calibrating a PMD, the method generally comprising (a) gathering calibration data about a person during one or more calibration periods; and (b) analyzing the calibration data to determine baseline data for the person, wherein the baseline data is configured to be compared against ambient data to determine a level of impairment of the person.

Normal (baseline) behavior and movement of the user may, in some aspects, be determined by the PMD through a combination of calibration and learning. Calibration may be used to facilitate the learning of the PMD. Calibration and learning may be, in some cases, not significantly different. In regards to some embodiments, calibration may be an initial period of time or amount of data necessary for the PMD to model an appropriate distribution for each behavior being monitored by the PMD.

In one aspect, before beginning the calibration period, if the user of the mobile device has been mandated by a court to utilize the device, the device may pull data, such as age, gender, height, weight, and race from penal system servers. If the use of the system is voluntary, the user may enter or edit this data from the settings interface of the system. This data may improve the accuracy of the system as it will allow the system to use the data gathered from external sources as parameters to create a context for the calibration and learning of the PMD. It should be noted that these examples are not intended to be limiting, and there will be numerous additional situations in which data may be mandated to be entered, data may be voluntarily entered, data may be drawn from other sources (such as social media), or otherwise.

Figure 4:
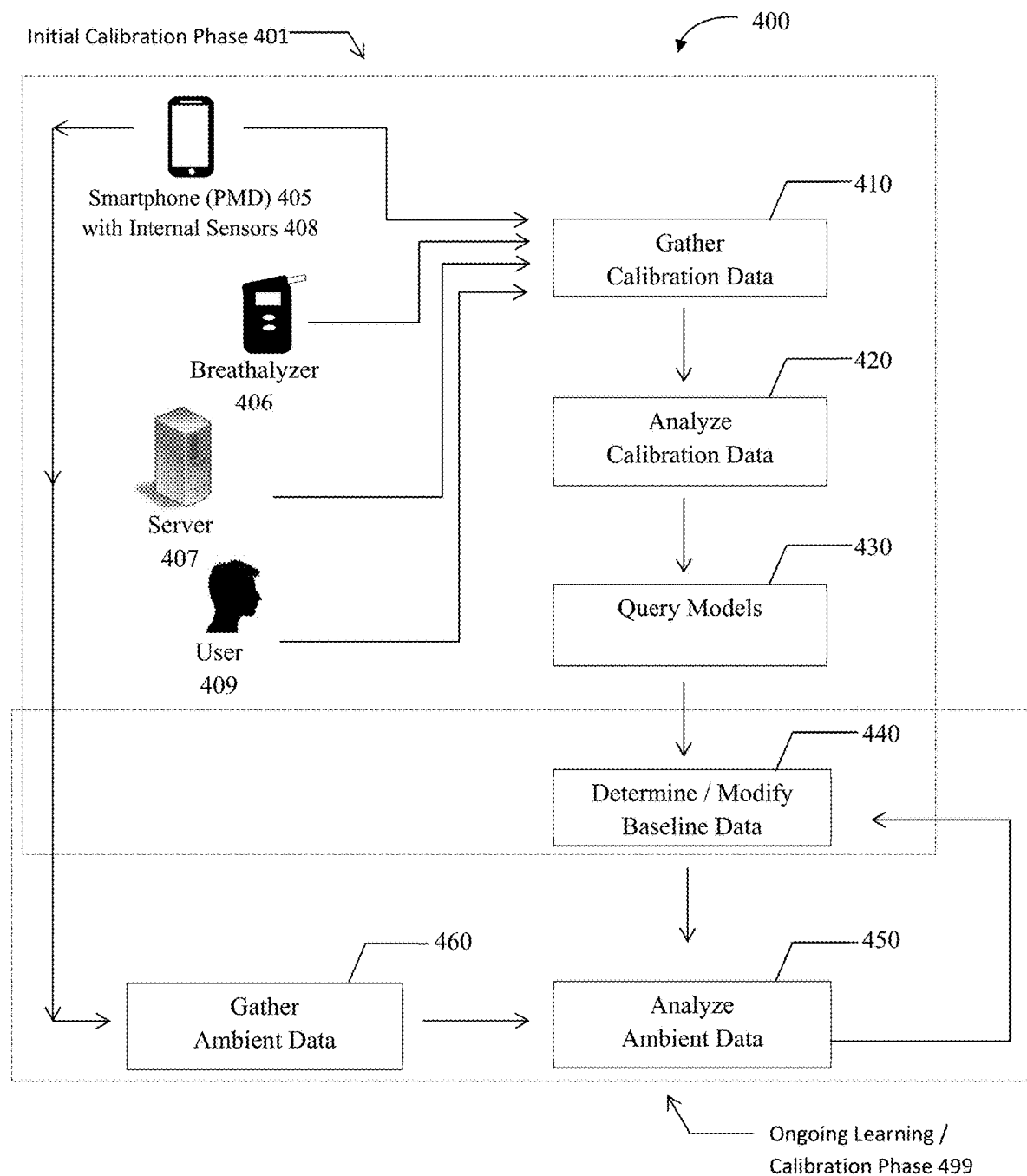
FIG. 4 schematically illustrates a method of calibrating a primary measuring device, comprising an initial calibration phase and an ongoing calibration phase according to an embodiment of the present invention.

Referring to FIG. 4, therein is shown an exemplary method 400 of calibrating a PMD. In the embodiment of FIG. 4, the method comprises an initial calibration phase 401 and an ongoing calibration phase 499. The initial calibration phase 401, begins at step 410, wherein calibration data is gathered from a smartphone (PMD) 405 having internal sensors 408, a breathalyzer 406, a server 407, and a user 409. The internal sensors 408 may comprise any number of sensors as described in methods 200 and 300 of FIGS. 2 and 3, respectively. Although the method of 400 of FIG. 4 is shown to gather data from internal sensors within the PMD 405, in other embodiments, calibration data may also be gathered from any number of external sensors as described in method 100 of FIG. 1 above. Likewise, and as described above in relation to FIG. 1, although the PMD of FIG. 4 is shown as a smartphone, the PMD may be any device capable of gathering, storing, analyzing and/or transmitting data.

At step 410 of the initial calibration phase 401, data is gathered from a breathalyzer 406. The breathalyzer 406, measures the actual level of intoxication of the user 409. By correlating the measurements from the internal sensors 408, as well as other data gathered by the PMD 405, with the blood alcohol level as measured by the breathalyzer 406, the data generated by the sensors on the PMD 405 may be identified as being generated while the user 409 had a set level of impairment. In some embodiments, a device that measures blood alcohol level may be part of or integral to the PMD 405.

In addition, step 410 may comprise gathering data from one or more servers (e.g., penal system servers, workplace servers, servers associated with social media sites, cloud based servers, etc.) to obtains data regarding the user 409. Some servers may provide such data without requiring permission of the user 409, whereas other servers/sites may require the user 409 to input username and/or password information in order to obtain access to the data. In some embodiments, medical data may be obtained regarding the user 409 with the appropriate permissions.

As part of the initial calibration process 401, the user 409 may be required to or may voluntarily input certain data. Such data may comprise body weight, anatomical gender, age, height, body mass index (BMI), race and/or other data. The anatomical gender of the user 409 is preferred over the gender that the user 409 identifies with, for the sake of anatomical and physiological accuracy. Blood alcohol content (BAC) tables are gender specific and as a result, the accuracy of the system in determining how easily the user 409 may become intoxicated is partially dependent on the correct gender input. The inputted data may be compared to a BAC table internal to the PMD 405, or a BAC table stored on a device or database remote from the PMD 405.

Gender is a useful parameter as there significant disparity between men and women's susceptibility to intoxication. For example, medical models for alcohol absorption indicate that premenopausal women get intoxicated faster than their male counterparts after drinking the same amount of alcohol. Additionally, the general recommended servings of alcohol are based on a 155-pound male having consumed three standard-sized beverages.

In addition to gender, when accounting for genetic or health based dispositions, such as the onset of menses, age is also an important parameter. For instance postmenopausal women metabolize alcohol at a much slower rate than younger women. However, in general there is a negative correlation between alcohol metabolism and increase in age across both sexes. This can be attributed to the fact that, in general, both aging of the body and the brain increase the propensity of the user 409 to experience the effects of chemical intoxication more rapidly.

Ethnicity is also a parameter that serves as an indicator of a consumer's predisposition to become intoxicated. Especially with regards to alcohol consumption, some ethnic groups (e.g., Asians) are predisposed to a deficiency in a key enzyme necessary for alcohol metabolism. In such ethnic groups, the lack of sufficient quantities of the enzyme acetaldehyde dehydrogenase, leads individuals in these groups to experience symptoms that they may find unpleasant after consuming small amounts of alcohol, whereas individuals outside these groups do not experience similar unpleasant symptoms until they become heavily intoxicated.

The size of the consumer, more specifically the body mass index (BMI) of the individual is a most critical parameter for which to account. Very simply, the greater the body mass, the greater the volume of blood necessary to nourish that body, and as a result, a larger individual can tolerate the same amount of alcohol far better than their less massive counterparts without feeling the effects. To calculate the BMI of the user 409 the system may use the height and weight data pulled from a server (e.g., server 407 of FIG. 4), derived from ambient data or sensors, or otherwise. This parameter is important because despite the fact that it is not completely accurate, it is the most consistent determiner across both genders. In other words, whether the user 409 is a big woman or a big man, they may feel the effects of intoxication slower than a smaller woman or a smaller man, in general. This is true because with the addition of every two pounds of weight, the blood volume of an individual increases a little over one percent. Percentage of body fat is also a significant factor that may be utilized in a similar manner. In one aspect, height, weight, and/or body fat percentage may be approximated by analysis of data from ambient sensors, or other data. For example, the appearance of the user 409 in a mirror or in a social media networking photograph may be used, optionally in conjunction with other objects that provide a scale, to determine height, weight and/or body fat percentage.

By obtaining such data, the device may be better able to determine additional data that is required or desirable or may be better able to determine the susceptibility of the user 409 to intoxication based on certain amounts of chemicals. In essence, the data may be utilized to provide a context by which the system may identify risks, identify data sets for comparison, and to otherwise analyze user information.

Referring again to FIG. 4, at step 420 calibration data is analyzed for patterns, similarities, correlations, other indicators, etc., as well as data that appears contrary to other data gathered that may suggest an error or anomaly. At step 430, models are queried and the data gathered is compared to charts and/or tables of impairment. At step 440, baseline impairment data is determined for the user 409. Step 440 completes the initial calibration stage. However, calibration and learning continue in the ongoing learning/calibration phase 499. At step 460, ambient data continues to be gathered from PMD 405 and its internal sensors 408. At step 450, the ambient data is analyzed and/or compared to baseline data, and baseline data may be modified based on the additional ambient data gathered and analyzed in the ongoing learning/calibration phase 499.

Although in the embodiment of FIG. 4, the ongoing learning/calibration phase 499 is only shown to modify baseline data based on additional ambient data gathered from the PMD 405, the ongoing learning/calibration phase 499 may also comprise comparing and adjusting baseline data based on additional data input by the user 409, additional data later acquired from one or more servers (e.g., server 407 of FIG. 4), and/or additional data later gathered from one or more external measurement devices (e.g., additional breathalyzer data, medical data from a blood glucose, BMI, blood pressure and/or heart rate monitor device, etc.)

In one aspect, during the device calibration phase or some other period, the user 409 may be required to walk (or measure while walking) a known distance and/or time interval with PMD 405 placed in a variety of known positions on the user's person. Alternatively, the PMD 405 may determine its position with some level of precision by utilizing measurements such as camera, noise (i.e. proximity to voice, breathing, or feet walking), triangulated signals, or other data. In this way the PMD 405 may be able to determine the normal gait of the user 409. For example, the PMD 405 may determine the normal gait of a user 409 while walking with the PMD 405 in his right pocket. In one aspect, the measurement may be based on walking at least approximately 350 yards on at least seven days.

The purpose of this is multifaceted. In some aspects, it is beneficial for the PMD 405 to be able to detect where the PMD (smartphone) 405 is on the user's person when a certain data input is observed for the user's gait. This may enable the PMD 405 to determine what data should be expected when the device is in a specific storage place on the user 409. The data inputs from the different clothing pocket or other storage points may be jointly utilized to comprise the user's gait profile. For a female, the smartphone may be placed in female specific storage locations such as the woman's purse during calibration.

After calibration, the PMD 405 may continue to record the user's gait. Through this recording, the PMD 405 may continue to measure and present an ever more accurate graphical representation of the user's gait. This measurement process may allow the PMD 405 to know the gait of the owner of the mobile device and differentiate the gait of its owner from other people. Furthermore, this continued measuring may allow the PMD 405 to adjust to occurrences affecting gait such as crippling injury. Ultimately, the PMD 405 may allow the device to know how it should expect to move if it is being carried by the user 409, and the certain storage point that the PMD 405 is being carried on by the user 409.

If the present gait reading of the user 409 consistently falls outside of the expected cycle function over a short interval of time, then the PMD 405 may return that the user's gait is abnormal and the user 409 may be losing his or her fine motor coordination and balance. The reason that the abnormal gait must be consistently sustained for at least a short interval of time is that the system must be able to overlook accidental stumbles and blunders. When referring to the abnormal gait as being consistently sustained for a short interval of time, it is not to suggest the abnormal gait pattern will return a wave-like function like the normal gait. Rather, it is meant that the gait consistently falls outside what has been determined to be the normal gait of the user 409. In one aspect, different baselines or calibration or executed gait may be utilized for different shoes or clothing.

It should be appreciated that while the discussion herein is with regard to measurement, calibration, and/or ongoing refinement of certain metrics (such as gait), the discussion is intended to be illustrative of other metrics as well. For example, the steadiness with which the PMD 405 is held, the appearance of the user 409 in video, or other factors would, in some aspects, be subject to a procedure similar to that described for gait.

Figure 5:
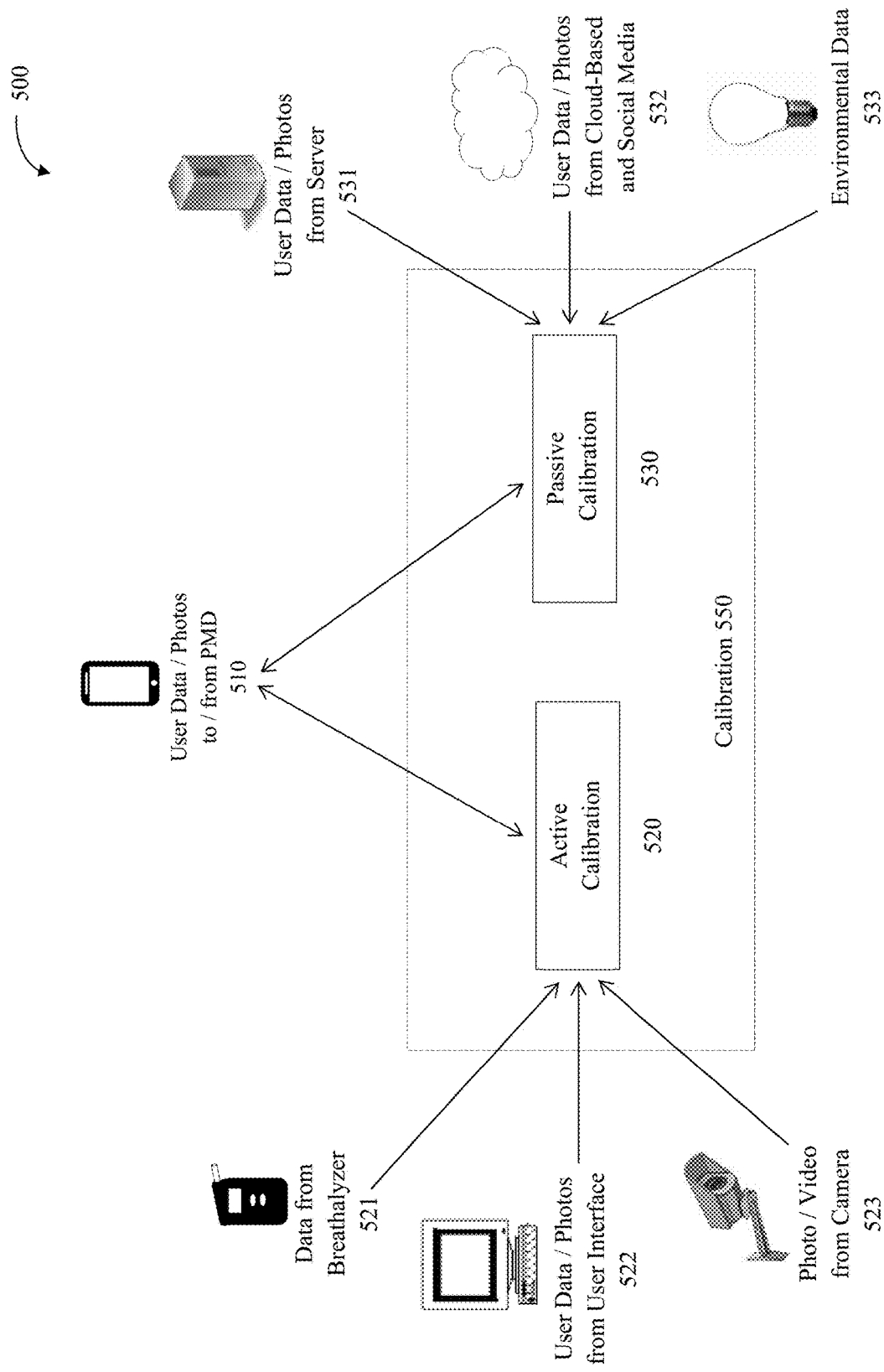
FIG. 5 schematically illustrates active and passive calibration phases according to an embodiment of the present invention.

Another phase of the initial and ongoing device data analysis refinement and calibration is facial recognition of a user. This calibration may be active, passive, or a combination. The system 500 of FIG. 5 schematically illustrates such active/passive calibration 550. In the embodiment if FIG. 5, the passive calibration phase 530 comprises gathering data/ user photos from a server 531, cloud-based storage systems and social media 532, as well as gathering environmental data 533. The active calibration phase 520 comprises gathering data from devices such as breathalyzer 521, data/ photograph(s) from a user interface 522 and photograph(s) and/or video from a camera 523.

In one embodiment, where use of the system 500 is mandated by penal code, initial data may be obtained when system 500 pulls one or more photos on file from a server 531 (e.g., a penal system server). In other cases, initial data/photo(s) may be obtained using a camera on the PMD 510, a camera 523 (e.g. on another PMD), photograph(s) from social media 532, photograph(s) stored on the PMD 510, or other sources. These initial photo(s) may be utilized to provide the PMD 510 with an initial frame of reference from which to identify the user in subsequently analyzed data.

Active calibration 520 may be available to the user from a user interface 522 of the system. Such calibration may be desirable in an instance in which, for some reason, the system 500 is having difficulty recognizing the user, such as when analyzing low resolution media. Additionally if the user is using the system 500 voluntarily and there is no initial photo for the system 500 to use as a reference, the system 500 may prompt the user to either upload one from their gallery or take a new photo. At which point the system 500 may behave as it does during active calibration 520. The active component of the calibration 520 would involve the user taking photos of themselves from different angles with the camera 523 as they are prompted to do so by the system 500.

Additionally the system 500 may pull media, such as photos of the user from other locations such as, but not limited to, public media streams, social media, and other cloud based media services 532. In addition, photographs and other measurements may be obtained from various sources, some of which do not require permission of the user and/or permission of the photographic source. In addition, in some embodiments, the system 500 may prompt the user to add data to photos as they are taken, such as identifying certain features of the user (e.g., the user's pupils), to identify the user's body parts (e.g., the user's hands), or other data.

In one aspect the system 500 may prompt the user for data input to help the system 500 make a decision such as identifying the user in a photo. For example, if photos or videos were captured at a family reunion, and the PMD 510 was used to take a photo or video containing the user and a sibling (or other person) with similar facial morphology, the system 500 could prompt the user, asking the user which person in the media is them. In another instance the system 500 may have difficulty locating key morphology that the facial, eye, pupil or other recognition algorithms may rely on and as a result the system 500 may prompt the user to touch the tip of their nose or select their eyes for instance.

The passive phase of the calibration 530, which would occur by default, would comprise analyzing photos and videos in the user's photo gallery on their mobile device (e.g., their smartphone/PMD 510). The passive component 530 of this calibration phase, like the active component 520, may allow the system 500 to learn what the user looks like. There are two reasons for the need for facial recognition capabilities in the system. The first reason is that the system 500 may need to tell the user apart from other people in a photo. Secondly, once the system 500 has determined who the user is in the photograph, the device may analyze facial features to determine health or impairment data, and in order to do so, it must be able to locate the facial features.

For example, the device 510 may find the user's eyes so it can measure the pupil dilation of the user. In order to accurately return meaningful data, for example, about the significance of the user's pupil dilation, the device 510 must be able to measure data source (for example, the change in pupil size). As a result there may, in some cases, be a minimum desired mega pixel specification for the camera of the device 510. In one aspect, the device 510 may aggregate a plurality of images in order to construct a high enough resolution composite image for analysis.

Additionally, the device 510 may determine whether the pupil size of the user is appropriate for the lighting of the environment that the user is in by gathering ambient data 533 in the passive calibration phase 530. Similarly, the device 510 may measure whether the user is listening to music or has the speaker for phone calls turned to a higher or lower volume than is normal for the situation.

The system 500 may improve recognition of a user by pulling photos from the user's gallery on their device 510 (or from other sources) and transforming the photo to different angles. In some cases, such as light field photography, such transformation may be accomplished utilizing a single photograph. Additionally the system 500 may pull videos from the device 510 or other sources and analyze each frame of the video in search of the user. When the user is found in a frame, the frame may be transformed like the standard photo. Once the face of the user has been detected and tagged, the system 500 may locate the user's eyes using a template based method. From that point the center of the user's radius may be found.

In one aspect, how bright the user is keeping the display of the PMD 510 may alert the system 500 of abnormal pupil function. Especially if the user overrides the screen brightness determined by the operating system of the PMD 510 by way of the ambient light sensor, the system 500 may compare the manually set screen brightness to the suggested brightness that the operating system may default to. As a result the system 500 may prompt the user with a pupil dilation test or a general eye movement test.

One mechanism by which the device 510 may obtain additional data is by measuring factors that are apparent in stored or live streamed video, audio, or images. For example, a user's gait may be apparent in a video taken and posted on Facebook™ or another social networking site. By analyzing the comments and other data related to the video, the system 500 may be able to infer the state of health and/or inebriation at the time the video was taken. The use of such external data may also be helpful in further calibration of the system 500 and/or in validating the inferences drawn from the motion data against actual video data. In some instances, the time at which the image or video was captured may be available (for example via metadata, via a watch in the image, or otherwise), and actual data captured by the PMD 510 may be compared to the image or video data in order to improve calibration of how the PMD 510 interprets data it measures. The location of the PMD 510 on the user may also be determined utilizing such external data sources.

Through the analysis of a number of photographs of the user in different environments, the system 500 may be able to determine that in a certain known lighting range, the user's pupil size should fall within a certain range of diameters. If the pupil size falls outside of the range for a known environment lighting range, the system 500 may return a message stating that the pupil size is abnormal and something may be wrong with the user.

An additional phase of device calibration may involve the device listening to the user as they speak, to learn how the user speaks normally. As a result the system 500 may be able to detect changes in the user's speech rate and volume. Once the system 500 has learned the way that the user speaks to a point of high accuracy, the system 500 may be able to determine when the user is speaking at a slower rate or when the user is speaking consistently louder than usual. Speech patterns may be analyzed with different people in different settings with different expectations. For example, a user may talk quietly and slowly with a child at night, but loudly and quickly while working at a restaurant.

The accuracy with which the system 500 can interpret what the user is saying may allow the system 500 to estimate when the user is slurring their speech, as the system 500 may not be able to understand the user. The system 500 may need to establish a voice profile for the user in which to store the properties of the user's speech. This may allow the system 500 to better ignore other unknown voices and ambient sounds. When the sounds of other voices and ambient sounds is too great and the system speech recognition accuracy has dropped critically low, the recognition feature may return an internal log stating that the environment is too loud, and suspend the speech recognition feature until the recognition ability accuracy of the system 500 reaches a threshold, such as one of 50% or more.

Features of the system that may not require calibration or may require less calibration are the sobriety tests. When the system 500 detects abnormal behavior, the system 500 may begin to time the periods between abnormal behavior readings. As the frequency of abnormal readings increases, the system 500 may increase the frequency with which it tests the capability of the user. The system 500 may test the capability of the user by prompting the user to take tests such as a copying a line of known text with the keyboard of the mobile device 510. This may actively test the user's fine motor function. The system 500 may also test the user by requesting that the user speaks a line of known text into the microphone of the mobile device 510. This may actively test the user's ability to speak. The system 500 may also test the user by flashing a string of four (or some other number of) characters on the screen of the mobile device 510. This exercise may test the user's memory.

Further, the system 500 may prompt the user to follow a brightly colored object (such as a ball) on the screen of the mobile device 510, and using the front facing camera and pupil detection algorithms, the system 500 may be able to detect the speed of the user's pupil movement. This may detect the speed of eye movement which is an important determiner of intoxication. In some aspects, the system 500 may be able to determine the user's pulse using the mobile device's cameras and/or an external heart rate monitor. Elevated and diminished pulses are good indications of intoxication when compared to the user's normal resting pulse. It should be appreciated that additional tests may be utilized and the description of tests herein is not limiting and is subject to change due to the availability of updated or new sensors that may be leveraged to gather more data or more accurate data.

In one aspect, the device 510 may recreate or emulate tests utilized by law enforcement to measure sobriety. For example, the device 510 may ask the user to walk in a straight line and utilize the ambient data sensors to determine the user's success. The device 510 may identify an existing straight line (such as the marking on a parking lot stall) or may, in the case of devices that can project images such as Google Glass®, create a virtual line. Similarly, the device 510 may ask a user to say the alphabet backwards and measure whether the user has accomplished the task in a manner consistent with a certain level of sobriety or impairment. Such tests may, in one implementation, be created as standalone applications that can be used on demand without incorporation into other aspects of the present invention.

The active sobriety tests may prompt the user as a text message does, and in some aspects may do so in a manner that is inconspicuous. Furthermore, in some aspects, each test may be constructed in a manner that takes no more than twenty to thirty seconds to complete. This falls within the timeframe that a text message may be sent or call may be made further decreasing conspicuousness. In another aspect, where a user has a wearable PMD that projects an image viewable only to the user (such as Google Glass®), the test may be one that does not require gross movement at all, such as a test where a user follows a dot with his pupil or blinks the answer to a math problem. In some embodiments, the number and/or rate at which the user makes errors in typing may be used as an indicator of the impairment of a person. Such tests may, in one implementation, be created as standalone applications that can be used on demand without incorporation into other aspects of the present-invention.

In order for the PMD 510 to function optimally, in some aspects the PMD 510 preferably gives any implementing program access to certain features, services and data on the PMD 510. The PMD 510 may need access, for example, to the GPS and location services, accelerometer, gyroscope, ambient light sensor, biometric sensors, microphone, cameras, photograph gallery and contacts. The PMD may also grant access to connected sensors, such as those connected via Bluetooth. In some aspects, where health or other sensitive information is accessed, such data may be encrypted, or an encryption system may be employed so as to protect such data and/or to comply with HIPAA and/or other government regulations.

The system 500 may need access to the location services of the mobile device 510 in order to detect when the user has entered a location such as a bar, liquor store or other establishments where alcohol may be procured. If the user remains in the location for more than a predetermined time interval (e.g., fifteen minutes), the system 500 may check the user into the location and assume that the user may be staying. The user may be automatically checked out of the location once the user has left the location or geofence. The accelerometer, gyroscope and ambient light sensor of the mobile device 510 are the sensors that may be leveraged to track measure and log the gait of the user. The cameras of the mobile device 510 may be used to measure and track the user's pupil dilation and movement speed, as well as the user's blood pressure. Access to a photo gallery on the mobile device 510 may allow the system 500 to strengthen the system's facial recognition and pupil tracking and measuring algorithms.

The feature requiring the most active input from the user is the BAC calculation feature. This feature allows the user to enter when they have had a drink and may track how many drinks the user has had over time while simultaneously, calculating the user's BAC using, for example, the user's gender and weight. The user may be able to input the drink consumed with the device keyboard and as the user is entering the drink, the system 500 may search its internal bartender guide database for a match. If a match in the database is found, the system 500 may pull the volume of alcohol from the drink recipe. If a match is not found, which is unlikely, the system 500 may default to approximation, assuming that the drink was 1.25 oz. of 80 proof liquor, 12 oz. of beer or 5 oz. of table wine. Alternatively or in addition, the system 500 may estimate the volume of alcohol based on a video of the drink preparation or by using chromatography to directly measure the volume of alcohol. Once the user has inputted the first drink the system 500 may continue to count the time intervals between drinks, setting the time of the first input as the top of the hour. From that point, the system 500 may be calculating the time interval between the current and subsequent drinks, and subtracting 0.01 BAC for every 40 minute interval between drinks.

With these different measures of intoxication signs recorded over time, from gait to pupil dilation, the instant system 500 may be able to compare the data of one recorded sign of intoxication to each of the data sets from the other sign categories in order to estimate the intoxication level of the person, or how far the person is from normal. This may be accomplished by comparing the determined levels of abnormality to the normal levels detected at calibration and through the system's learning.

In some instances, when the system 500 is collecting data for the various signs of intoxication, the system 500 may be able to graph the data of the perceived intoxication over time. As a result, the user or administrator may be able to look at a graph generated by the system 500 and learn approximately how intoxicated the user was at a given time. Each data point on the graph may retain additional information such as the location that the user was at that intoxication measurement. As a result, clicking a data point on the graph may present the user or administrator with a breakdown of the available intoxication measures for that point, allowing the user or administrator to have a better understanding of how the user progressed over a particular time interval. The system 500 may also present the data of the different signs, such as loss of fine motor control, loss of balance, slurred speech or alteration in intonations, fluctuation in vital signs and changes in pupil size and response times side by side, to create dashboard summary of how the user was progressing as the user consumed alcohol over time.

The system 500 also has the ability to send notifications to predetermined contacts. For instance, if the user is on parole, the system 500 would be able to notify the user's parole officer and appropriate department of the precinct. If the user is in a rehabilitation program, the system 500 would be able to notify the user's sponsor. Likewise, if the system 500 is being used voluntarily by a person trying to be more responsible, the system 500 can notify the user's friends of the user's state of intoxication. For example the system 500 may send a user's friend a notification stating that "your friend is getting very intoxicated; you may want to check on them," while simultaneously notifying the user with a message stating that "you are dangerously intoxicated." Furthermore the system 500 may notify the user when the user has reached the legal limit of intoxication.

In addition to the notifications, the system 500 can communicate with other devices. Just like mobile devices can communicate with cars over Bluetooth to let the car know of an incoming message or call, among other notifications, the instant system 500 can alert the vehicle, making it aware that the driver is unfit to drive because of their BAC. In some instances, the notification may even disable the vehicle, preventing the user of the system 500 from operating the vehicle.

In a non-alcohol related example, colon cancer risk or other digestive issues may be better evaluated by measuring the time the person is on the toilet as well as the amount and type of interaction with the device during that period. Indeed, the time between when the user stops interacting with the device and when the device (via accelerometer or otherwise) determines the user is walking out of the bathroom may be used to determine the amount of cleanup required and therefore provide a proxy for the firmness of the user's stool. The sound of toilet paper being pulled and/or the sound of the toilet being flushed and/or the sound of the waste hitting the toilet water may all also be utilized to determine certain health factors.

In one aspect, abrupt changes to measured data may indicate that the device has been stolen. In another aspect, multiple profiles may be created for multiple users of the device. Such profiles may be shared within affinity or other groups. For example, a husband and wife may periodically hold the phone of the other, and the phone would recognize that it is now following the pattern of data associated with the spouse.

Perceivable or not by the affected person, there are a host of effects that a drug such as alcohol may have on an individual. Some of the measurable signs of intoxication are loss of fine motor control, loss of balance, slurred speech or alteration in intonations, fluctuation in vital signs, nystagmus, and changes in pupil size and response times. Some of these signs are passively measurable, such as the loss of balance, which affects one's gait. Additionally, speech can be passively measured. One factor relating to measurability is whether the data presents itself in similar repetitive cycles resulting in a sine wave-like function, although the absence of such cycles does not make a sign of intoxication unmeasurable.

Exemplary Systems/Devices for Determining the Level of Impairment

Aspects of the present invention also relate to systems and devices to estimate the level of impairment of a person. In an exemplary embodiment, the device comprises (a) one or more sensors operably coupled to a first PMD, the sensors configured to capture ambient data about a person, wherein the first PMD is configured to query at least one data base to identify baseline data and compare the ambient data to the baseline data to determine the likelihood that the person is impaired.

Figure 6:
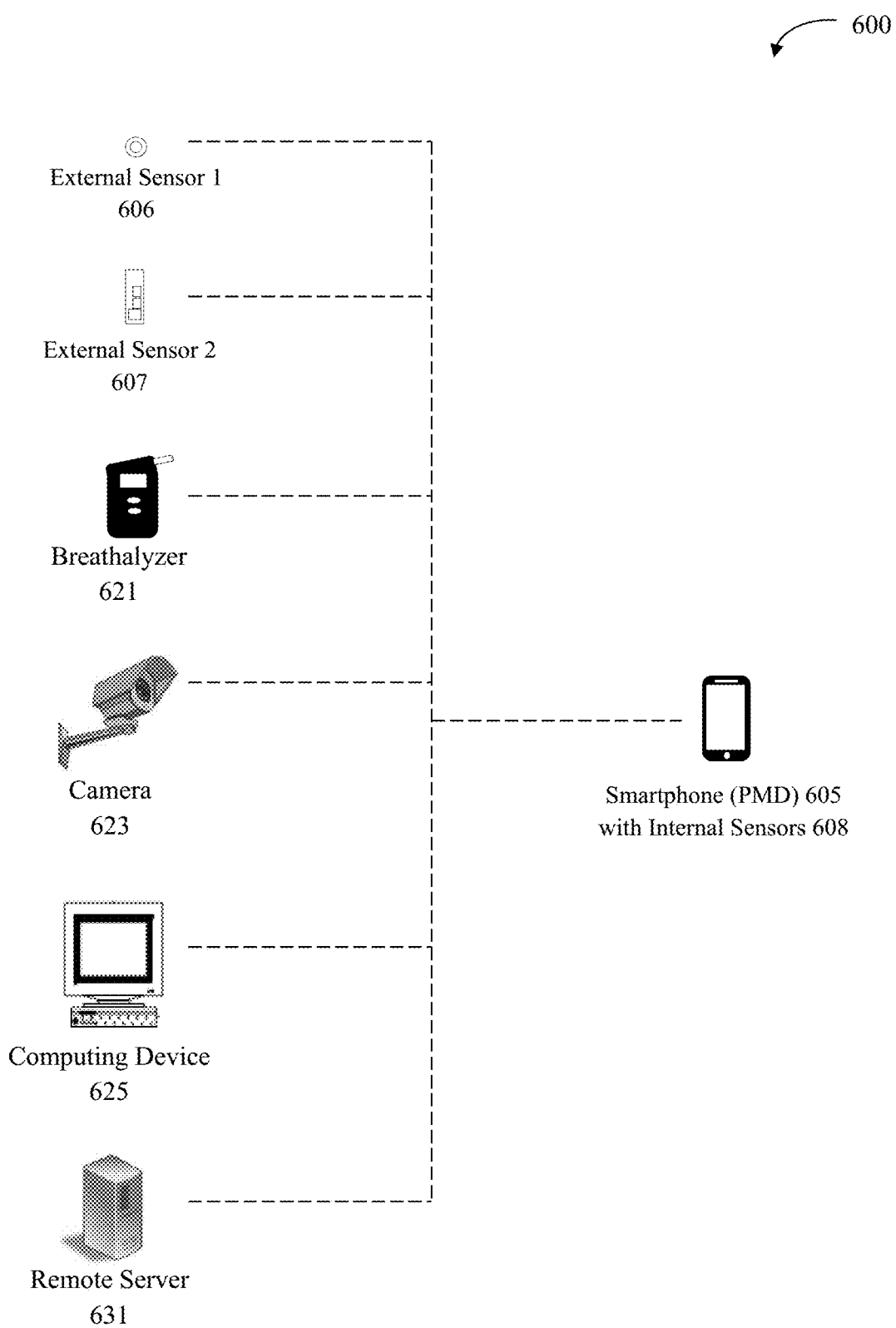
FIG. 6 schematically illustrates a system, including various devices, for determining the likelihood that a person is impaired

Referring now to FIG. 6, therein is shown an embodiment of a system 600 for estimating the level of impairment of a person. In the embodiment of FIG. 6, a smartphone (first PMD) 605 having internal sensors 608 is operably coupled to external sensors 606 and 607, external measuring device (breathalyzer) 621, camera 623, computing device 625 and remote server 631. The internal sensors 608 of first PMD 605 may comprise one or more sensors, including, but not limited to a fingerprint sensor, an accelerometer, a three-axis gyroscope, a compass, an assisted GPS, a charging sensor, a battery measurement sensor, an ambient light sensor, a magnetometer, an proximity sensor, an orientation sensor, and/or one or more biometric sensors.

In some embodiments, other data collection devices may also be integral to the first PMD 605. For example, the first PMD 605 may also comprise a front facing camera (with associated sensors), a rear facing camera (with associated sensors), a microphone, a digitizer (e.g., a touch screen), etc. Further, the first PMD 605 may have capabilities to capture other data, including, but not limited to cellular voice, cellular data (e.g., usage history), WiFi data (e.g., internet sites visited) and/or Bluetooth data, and store and/or transmit data.

The first PMD 605 may optionally be equipped with one or more of a variety of other sensors, including, but not limited to a wireless charging station (and associated sensors), terrestrial/RDS/satellite radio sensors, pressure sensors, temperature sensors, humidity sensors, CO sensors, $CO_2$ sensors, NFC communications sensors, face and object detection devices (e.g., within software supporting camera), and/or barometric pressure sensors.

In the embodiment of FIG. 6, each of first and second external sensors 606, 607 may be one of the many types of sensors listed above as sensors possibly internal to the first PMD 605, except that external sensors 606 and 607 reside external to the PMD. Additionally, optional external measurement device (breathalyzer) 621 is also coupled to first PMD 605. Although the external measuring device 621 of FIG. 6 is a breathalyzer, in other embodiments, one or more such external devices may include, but are not limited to devices to measure blood alcohol level, blood sugar level, blood pressure, heart rate, activity level, calorie consumption, etc.

In the embodiment of FIG. 6, the first PMD 605 is operably coupled to a computing device 625, in which data may be analyzed, identified and/or stored. However, in other embodiments, the data may be analyzed, identified and/or stored on first PMD 605 and/or the first PMD 605 may be operably coupled to one or more servers 631 or other storage devices (e.g., a zip drive, thumb drive, CD ROM, DVD, etc.) from which the first PMD 605 may pull useful data. Additionally, the first PMD 605 may be operably coupled to one or more cloud storage databases (not shown). Operably coupling may comprise, directly coupling the external sensors, measuring device(s), servers and/or storage devices or may comprise coupling via near field communication, Bluetooth, local area network, Wi-Fi network, cellular network, wide area network, etc.

Although not shown in the embodiment of FIG. 6, the system 600 may also comprise a second PMD operably coupled to the first PMD 605, wherein the second PMD and the first PMD 605 share data with each other. In some embodiments, the second PMD is configured to process the ambient data shared by the first PMD 605. In some embodiments, a plurality of PMD's may be operably coupled to the first PMD 605, and the plurality of PMD's may share data with each other and/or the first PMD 605. In some embodiments, one or more of the plurality of PMD's may be configured to process the ambient data shared by the first PMD 605.

In some embodiments, the first PMD 605 may also comprise a transmitter, and the transmitter may be configured to transmit notifications to one or more predetermined contacts. For example the system 600 may send a user's friend a notification stating that "your friend is getting very intoxicated; you may want to check on them," while simultaneously notifying the user with a message stating that "you are dangerously intoxicated." Furthermore the system 600 may notify the user when the user has reached the legal limit of intoxication.

The foregoing descriptions of specific embodiments of the present invention have been presented for purposes of illustration and description. They are not intended to be exhaustive or to limit the invention to the precise forms disclosed. Obviously, many modifications and variations are possible in light of the above teaching. The embodiments were chosen and described in order to best explain the principals of the invention and its practical application, to thereby enable others skilled in the art to best utilize the invention and the various embodiments and modifications as are suited to the particular use contemplated. It is intended that the scope of the invention be defined by the components and elements described herein and their equivalents.

What is claimed is:

1. A device for detecting changes to user interactions with a user interface, the device comprising:
   one or more sensors operably coupled to a primary monitoring device ("PMD");
   the sensors comprising one or more of a touch screen, an input device, a gyroscopic sensor, an attitude sensor, a microphone, a camera and a motion sensor;
   the PMD monitoring at least one of the sensors to detect user errors in interaction with the device;
   the device querying one or more databases for database data and comparing an error rate with the database data, the database data containing one or more of measurements of error rates of other persons; past error rates of the current user; projected error rates based on physiological characteristics of the user, and/or any of the foregoing when read in an environment with comparable amount of ambient noise; and
   the device identifying a level of difference between the database data and the error rate.

2. The device of claim 1, wherein the error rate is compared to a second database, which database contains physiological changes and associated error rates (the "Association").

3. The device of claim 2, wherein the user is alerted to one or more of the physiological changes identified by the Association.

4. The device of claim 2, wherein one or both of the error rate and the Association is provided to at least one of the user, a drug recovery program sponsor, and a health care provider.

5. The device of claim 2, wherein one or both of the error rate and the Association is provided to a parent or a guardian of the user.

6. The device of claim 2, wherein the user is alerted to one or more of the physiological changes identified by the Association when the physiological change is greater than one sigma deviation from normal when compared to one or more database measurement sources.

7. The device of claim 6, wherein one or both of the error rate and the Association is provided to at least one of the user, a drug recovery program sponsor, and a health care provider.

8. The device of claim 1, wherein error measurement is compared to data limited by one or more of location, ambient sound, or time of day.

9. A device for detecting changes to verbal cadence, the device comprising:
   one or more sensors operably coupled to a primary monitoring device ("PMD");
   the sensors comprising one or more of a microphone, a gyroscopic or non-gyroscopic device capable of measuring movement caused by sound waves;
   the PMD monitoring at least one of the sensors to detect a rhythmic and/or wave-like function (the "Cadence") generated by a user's voice;
   the device querying one or more databases for database data and comparing the Cadence with the database data, the database data containing one or more of measurements of other persons; past measurements of the current user; projected measurements based on physiological characteristics of the user; or measurements of other users; and
   the device identifying a level of difference between the database data and the Cadence (the "Change").

10. The device of claim 9, wherein the Change is compared to a second database, which database contains physiological changes and associated measurements of a change to voice cadence (the "Second Association").

11. The device of claim 9, wherein the Change is determined only by comparison to database entries made in an environment with a comparable amount of ambient noise.

12. The device of claim 9, wherein the user is alerted to one of more of the physiological changes identified by the Second Association.

13. The device of claim 9, wherein one or both of the Second Association and the Change is provided to one or both of the user and a health care provider.

14. The device of claim 9, wherein one or both of the Second Association and the Change is provided to a parent or guardian of the user.

15. The device of claim 9, wherein the user's voice detected is compared to data regarding voice patterns to determine an identity of the speaker.

16. A device for detecting changes to a user's balance, comprising:
   one or more motion sensors operably coupled to a PMD;
   the PMD monitoring and saving data from the sensors, where such data is consistent with a fall or other loss of balance (an "Episode");
   the device determining whether a number of Episodes taking place over a set period of time exceed a threshold number;
   where the threshold number is different for different levels of magnitude of Episodes.

17. The device of claim 16, wherein the different levels of magnitude of Episodes requires at least a one sigma deviation from normal.

18. The device of claim 16, wherein the different levels of magnitude of Episodes requires at least a two sigma deviation from normal.

* * * * *